United States Patent [19]

Millerd et al.

[11] Patent Number: 4,581,014

[45] Date of Patent: Apr. 8, 1986

[54] FLUID INFUSION SYSTEM

[75] Inventors: Donald L. Millerd; Robert S. Alpert; John E. Kling, all of San Diego, Calif.

[73] Assignee: Ivac Corporation, San Diego, Calif.

[21] Appl. No.: 596,279

[22] Filed: Apr. 3, 1984

[51] Int. Cl.⁴ .............................................. A61M 5/14
[52] U.S. Cl. ..................................... 604/80; 604/248
[58] Field of Search ................................. 604/80–85, 604/246, 248, 32

[56] References Cited

U.S. PATENT DOCUMENTS

| | | |
|---|---|---|
| 1,664,046 | 3/1928 | Rosenberg . |
| 2,538,215 | 1/1951 | Stack ..................................... 604/32 |
| 2,866,457 | 12/1958 | Moore . |
| 2,999,499 | 9/1961 | Willet . |
| 3,157,201 | 11/1964 | Littmann ........................ 604/32 X |
| 3,254,647 | 6/1966 | Vogel . |
| 3,369,708 | 2/1968 | Hein . |
| 3,783,895 | 1/1974 | Weichselbaum . |
| 3,831,813 | 8/1974 | Latham, Jr. . |
| 3,938,520 | 2/1976 | Scislowicz et al. . |
| 3,949,745 | 4/1976 | Howell . |
| 3,957,082 | 5/1976 | Fuson et al. ........................ 604/80 |
| 3,976,068 | 8/1976 | Lundquist . |
| 4,000,742 | 1/1977 | DiGiacomo . |
| 4,211,588 | 7/1980 | Raines . |
| 4,217,894 | 8/1980 | Franetzki . |
| 4,236,515 | 12/1980 | Genese . |
| 4,392,850 | 7/1983 | Elias et al. . |
| 4,392,851 | 7/1983 | Elias . |
| 4,410,321 | 10/1983 | Pearson et al. . |
| 4,411,662 | 10/1983 | Pearson . |

OTHER PUBLICATIONS

Vacuum Vial Infusion System, filed Dec. 5, 1983, Ser. No. 558,060.
Controlled Release Infusion System, filed Jul. 5, 1983, Ser. No. 514,268.
Intravenous Administration System For Dry Medicine, Ser. No. 401,874, filed Jul. 26, 1982.

*Primary Examiner*—John D. Yasko
*Attorney, Agent, or Firm*—Fulwider, Patton, Rieber, Lee & Utecht

[57] ABSTRACT

A fluid infusion system includes a selector valve for convenient interruption of administration of a primary infusion fluid to a patient to permit administration of a secondary infusion fluid, such as a selected drug solution, followed by resumption of primary fluid flow. The selector valve includes a valve housing with a primary spike for connection to a primary fluid container, a dual path secondary spike for connection to a vial or the like containing the secondary infusion fluid, and an outlet fitting for connection to the patient, for example, through a standard intravenous (IV) infusion set. A valve insert is movably mounted within the valve housing and defines a fluid channel network for controlling flow from the primary and secondary spikes to the outlet fitting. In one form, the valve insert is movable between a first position routing the primary infusion fluid directly from the primary spike to the outlet fitting for supply to the patient, and a second position routing the primary infusion fluid through the secondary spike and the vial to wash the secondary infusion fluid therefrom through the outlet fitting for flow to the patient. In an alternative form, the valve insert is movable to an intermediate position for coupling the primary infusion fluid through the secondary spike to a vacuum vial for reconstituting, for example, a dried pharmaceutical therein without supply to the patient, after which the valve insert is movable to the second position permitting fluid flow from the vial to the outlet fitting. Upon completion of secondary infusion fluid administration, primary fluid administration resumes automatically by flow thereof through the vial and outlet fitting to the patient.

44 Claims, 18 Drawing Figures

FLUID INFUSION SYSTEM

BACKGROUND OF THE INVENTION

This invention relates generally to systems and devices for use in the infusion of medical liquids into a patient. More particularly, this invention relates to an improved fluid infusion system for controlled and selected administration of a primary infusion fluid and a secondary infusion fluid to a patient.

A variety of medical liquids are commonly administered intravascularly to a patient in the course of medical treatment. Such medical liquids can include, for example, saline or dextrose solutions or other fluids for correcting body chemistry imbalances or medical solutions prescribed for treatment of disease. These medical liquids are normally available commercially in aseptic containers having self-sealing caps of a resilient material adapted to be punctured by an appropriate instrument, such as a hypodermic needle for removing the fluid contents for supply to the patient.

Infusion of medical liquids is normally carried out by use of a so-called intravenous administration set, sometimes referred to as an IV set, which includes means for puncturing the self-sealing cap of the fluid container and means for guiding the fluid in a continuous regulated flow to a catheter or the like inserted, for example, into the vein of a patient. Such IV sets typically include a drop former having a spiked conduit at one end for insertion into the fluid container which is normally supported in an inverted position above the patient. The drop former converts fluid flowing from the container into a progression of drops which fall through a transparent drop chamber for visual observation by medical personnel or detection by appropriate electronic instrumentation to confirm the presence and rate of fluid flow. The drops collect within a lower region of the drug chamber for flow into a flexible and normally transparent length of plastic tubing connected in turn to the intravenous catheter. Flow rate control devices, such as a manually adjustable roller clamp or automated flow control instrument, are provided along the length of the plastic tube to control the rate of fluid delivery to the patient.

In many instances, during infusion of a medical liquid into a patient, it is necessary or desirable to administer a prescribed quantity of a different or second medical fluid. For example, during infusion of a saline or dextrose solution, it may be necessary to administer a small quantity of a selected drug solution to the patient. This second medical fluid can be administered via a separate intravenous access site by use of a hypodermic syringe or an additional IV set, but such techniques undesirably require additional needle punctures in the patient to increase patient trauma, both physically and emotionally. Accordingly, it has generally been desirable to administer such additional medical fluids through the plastic tubing and catheter of the in situ IV set.

To accommodate occasional administration of a secondary infusion fluid, modern IV sets commonly include a so-called Y-site fitting installed along the length of the plastic fluid flow tubing. The Y-site fitting comprises a primary conduit connected in-line with the plastic tubing for normal passage of the primary infusion supplied to the patient, in combination with a short branch conduit having a free end closed by a self-sealing resilient cap. According to conventional techniques, the secondary infusion fluid can be injected through the self-sealing cap of the Y-site fitting by use of a hypodermic syringe, but such techniques are not particularly well suited for infusing the secondary fluid over a prolonged time period. Alternatively, the secondary infusion fluid can be injected into the Y-site fitting through a hollow needle which in turn is connected through an auxiliary IV set to a secondary fluid container suspended typically for gravitational flow at a height greater than the primary fluid container. This latter technique, however, incorporates a number of significant disadvantages, including, for example the requirement of a relatively high degree of attention and manipulation by medical personnel, together with increased costs associated with the use of an auxiliary IV set and specially adapted primary IV sets including a check valve to prevent inadvertent backflow of the secondary fluid into the primary fluid container.

A number of other fluid infusion systems and devices have been proposed in attempts to accommodate facilitated and cost-effective introduction of a secondary infusion fluid into an in situ IV set. These system proposals generally envision specialized adapter fittings in-line with the plastic tubing of the IV set wherein a secondary fluid container can be connected when desired to the adapter fitting to supply the secondary fluid through the tubing to the patient. In general, however, these proposed systems have been relatively complex in construction and have required a number of manipulative steps including halting of primary fluid flow preparatory to administration of the secondary infusion fluid. These manipulative steps require considerable skill of medical personnel and further must be performed hurriedly to prevent activation of alarm devices sensing the absence of fluid flow through the drop former device of the IV set. Accordingly, these proposed infusion systems generally have not achieved any significant degree of consumer acceptance.

There exists, therefore, a significant need for an improved fluid infusion system including relatively simple, inexpensive, easy-to-use, and preferably disposable apparatus facilitating occasional interruption of primary infusion fluid administration to permit infusion of a selected secondary fluid followed by automatic resumption of primary fluid flow. The present invention fulfills these needs and provides further related advantages.

SUMMARY OF THE INVENTION

In accordance with the invention, an improved fluid infusion system includes a relatively simple and easy-to-use selector valve for controlling administration of primary and secondary infusion fluids to a patient, wherein those fluids are administered through a single intravenous (IV) infusion set. The selector valve is movable between a first position coupling the primary infusion fluid directly to the IV set for flow to the patient, and a second position coupling the primary infusion fluid for flow into a removably mounted secondary fluid container to wash the secondary infusion fluid therefrom for flow through the IV set to the patient.

In the preferred system, the selector valve comprises a valve housing having an upstanding primary spike for piercing the self-sealing cap of an inverted primary infusion fluid container. The valve housing further includes a generally upstanding dual path secondary spike for piercing the self-sealing cap of a generally inverted secondary infusion fluid container, such as a small vial of standardized size containing a selected drug solution.

An outlet fitting on the valve housing is adapted for connection to the upper end of a drop chamber of the IV set, wherein this drop chamber in turn has a lower end connected to a length of flexible tubing for infusion fluid supply to the patient.

The selector valve further includes a valve insert movably carried within the valve housing and including a fluid channel network for controlling fluid flow through the selector valve. In a first position, the fluid channel network is oriented to permit flow of the primary infusion fluid directly from the primary spike to the valve housing outlet fitting for supply through the IV set to the patient. In this first valve insert position, flow of the primary infusion fluid to the secondary spike is prevented. In a second position of the valve insert, the fluid channel network is reoriented to block direct flow of the primary infusion fluid to the outlet fitting. Instead, the primary infusion fluid flow is coupled to one path of the dual path secondary spike for passage into the secondary fluid container, whereas the other secondary spike path is coupled to the valve housing outlet fitting. The secondary container is thus coupled in series with the primary fluid flow path such that the primary infusion fluid washes the secondary fluid from the secondary fluid container through the outlet fitting and the IV set to the patient. When secondary fluid infusion is completed, primary infusion fluid flow continues through the secondary fluid container to the patient. Conveniently, position indicating means such as a bead on the valve insert seatable within notches in the valve housing are provided for releasable supporting the valve insert in the first and second rotational positions.

In an alternative preferred form of the invention, the selector valve insert is rotatable to a third position intermediate the first and second positions as descibed above. In this intermediate position, the valve insert blocks the valve housing outlet fitting to interrupt fluid flow to the patient while coupling the primary infusion fluid flow to the secondary spike. Accordingly, an evacuated secondary fluid container may be filled with primary infusion fluid to reconstitute, for example, a dried pharmaceutical therein to form the secondary infusion fluid for supply to the patient when the valve insert is rotated to the second position.

Other features and advantages of the present invention will become more apparent from the following detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
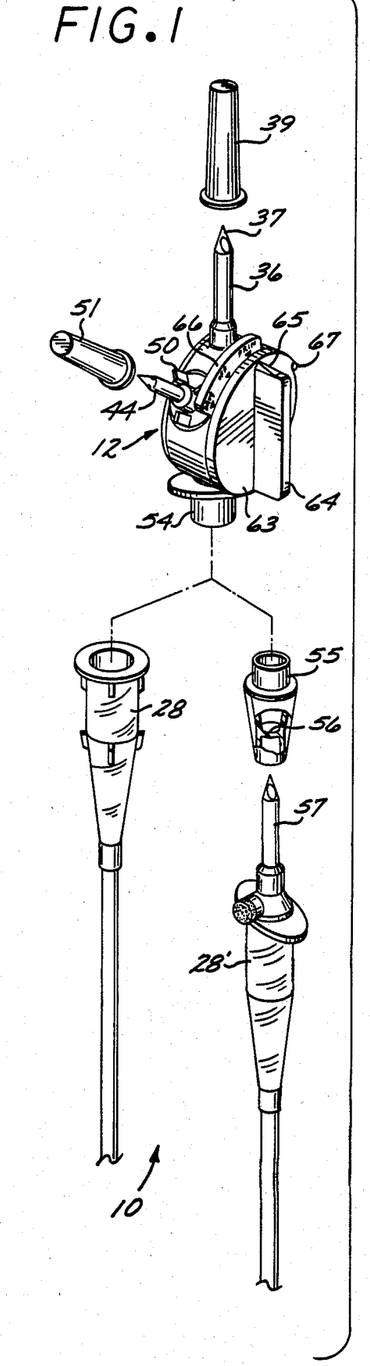
FIG. 1 is an exploded perspective view illustrating principal components of a fluid infusion system embodying the novel features of the invention.
Figure 2:
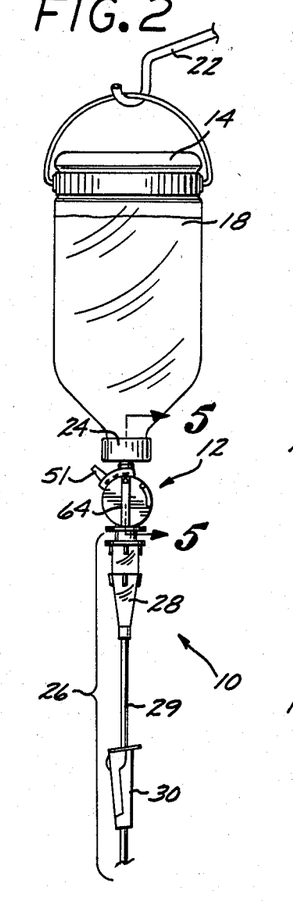
FIG. 2 is a front elevation view depicting the infusion system with a selector valve in a first position for normal administration of a primary infusion fluid to a patient.
Figure 3:
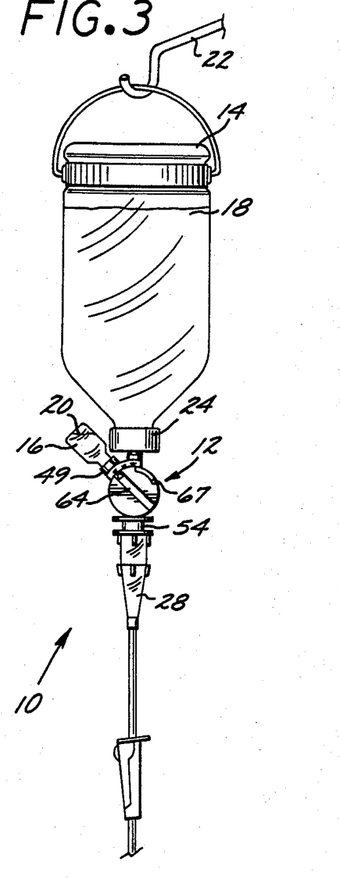
FIG. 3 is a front elevation view depicting the infusion system with the selector valve in a second position for administration of a secondary influsion fluid to a patient.

As shown in the exemplary drawings, a fluid infusion system referred to generally by the reference numeral 10 is provided for controlled interruption of administration of a primary infusion fluid to a patient to permit administration of a secondary infusion fluid, such as a selected drug solution, followed by resumption of primary infusion fluid flow. The fluid infusion system 10 includes a relatively simple, economical, and easy-to-use selector valve 12 for connection to a primary fluid container 14 and for removable connection to a secondary fluid container 16, as shown in FIGS. 2 and 3. The selector valve 12 is movable between a first or primary position (FIG. 2) for coupling primary infusion fluid 18 directly to a patient (not shown) and a second position (FIG. 3) wherein secondary infusion fluid 20 is administered to the patient.

The fluid infusion system 10 of the present invention advantageously provides simplified and economical system components having a high degree of compatibility with existing equipment used in the administration of medical liquids to patients. The present invention can thus be incorporated into existing fluid infusion systems and equipment and further can be operated by medical personnel with little or minimal preparatory training. In use, the infusion system 10 including the selector valve 12 provides a highly convenient means and method for occasional infusion of a secondary infusion fluid, such as a selected drug solution, by flow-coupling the secondary fluid in-line into an in situ intravenous (IV) fluid administration set. When administration of the secondary infusion fluid is completed, primary infusion fluid flow resumes automatically without requiring attention or intervention by medical personnel.

As shown generally in FIGS. 2 and 3, the fluid infusion system 10 is incorporated into and used in combination with a number of standard fluid administration system components. More particularly, the primary fluid container 14 may comprise any standard infusion fluid container such as a bottle or bag containing saline, dextrose, or other selected primary infusion fluid 18. This primary fluid container 14 is conventionally suspended in an inverted position from a support stand 22 at a vertical elevation above the patient. When inverted, the primary fluid container 14 has a lower cap 24 including a self-sealing resilient member 25 (FIG. 6) through which the primary infusion fluid 18 may be drawn by gravitational forces for administration to the patient.

According to conventional infusion fluid administration techniques, the primary infusion fluid 18 is coupled to the patient by a so-called fluid administration set 26, commonly referred to as an IV set. This IV set 26 includes a drop former (not shown) for receiving the primary infusion fluid flow and for converting that fluid flow into a regular progression of drops. These fluid drops fall through a transparent drop chamber 28 where they can be observed visually by medical personnel, or alternatively, by electronic drop sensing equipment used to confirm and/or control fluid flow through the IV set. The fluid drops collect within the drop chamber 28 for flow through flexible and typically clear plastic tubing 29 which in turn is connected to an appropriate catheter or other hypodermic device (not shown) adapted for intravenous or intra-arterial insertion into the patient. A flow control device such as the illustrative roller clamp 30 depicted in FIG. 2 is mounted along the tubing 29 and is adjustable to control the flow rate of infusion fluid through the tubing. Alternatively, a commerically available automated flow control instrument or pump (not shown), may be used to control fluid flow rate through the plastic tubing 29.

In accordance with the invention, the selector valve 12 is mounted preferably between the primary fluid container 14 and the drop chamber 28 of the IV set 26. In this position, the selector valve 12 may be set rapidly and easily to a first or primary position coupling the primary infusion fluid 18 for direct flow through the selector valve 12 into the IV set 26 for administration to the patient. Alternatively, the selector valve may be switched rapidly to the second position illustrated in FIG. 3 when the secondary fluid container 16 is mounted thereon. In this second position, the selector valve 12 diverts the primary infusion fluid 18 for flow into and through the secondary fluid container 20 prior to communication with the IV set 26, thereby washing the secondary infusion fluid 20 into the IV set for administration to the patient.

The selector valve 12 is shown in more detail in one preferred form in FIGS. 1 and 4-8. As shown, the selector valve comprises a generally cylindrical valve housing 32 formed from a suitable molded plastic material or the like to define a central valve chamber 33 of generally cylindrical shape. The valve housing 32 is oriented normally in use with its central axis 34 (FIG. 5) disposed generally in a horizontal plane. An upper fluid inlet port 35 is formed through the cylindrical housing 32 and includes an externally open counterbore for seated reception of the base end of a primary spike 36, which may also be formed from molded plastic or the like. This primary spike 36 projects upwardly and terminates in a sharp free end 37 for puncture reception upwardly through the self-sealing resilient member 25 of the primary fluid container cap 24. Importantly, this primary spike 36 is hollow to provide an open conduit 38 for passage of the primary infusion fluid 18 downwardly through the spike into the valve chamber 33 of the selector valve 12, as will be described in more detail. A protective cap 39 (FIG. 1) is conveniently provided for seated reception over the primary spike 36 to maintain sterility thereof until the selector valve 12 is ready for use.

Figures 6, 7, 8, 9, 10, 11, 12:
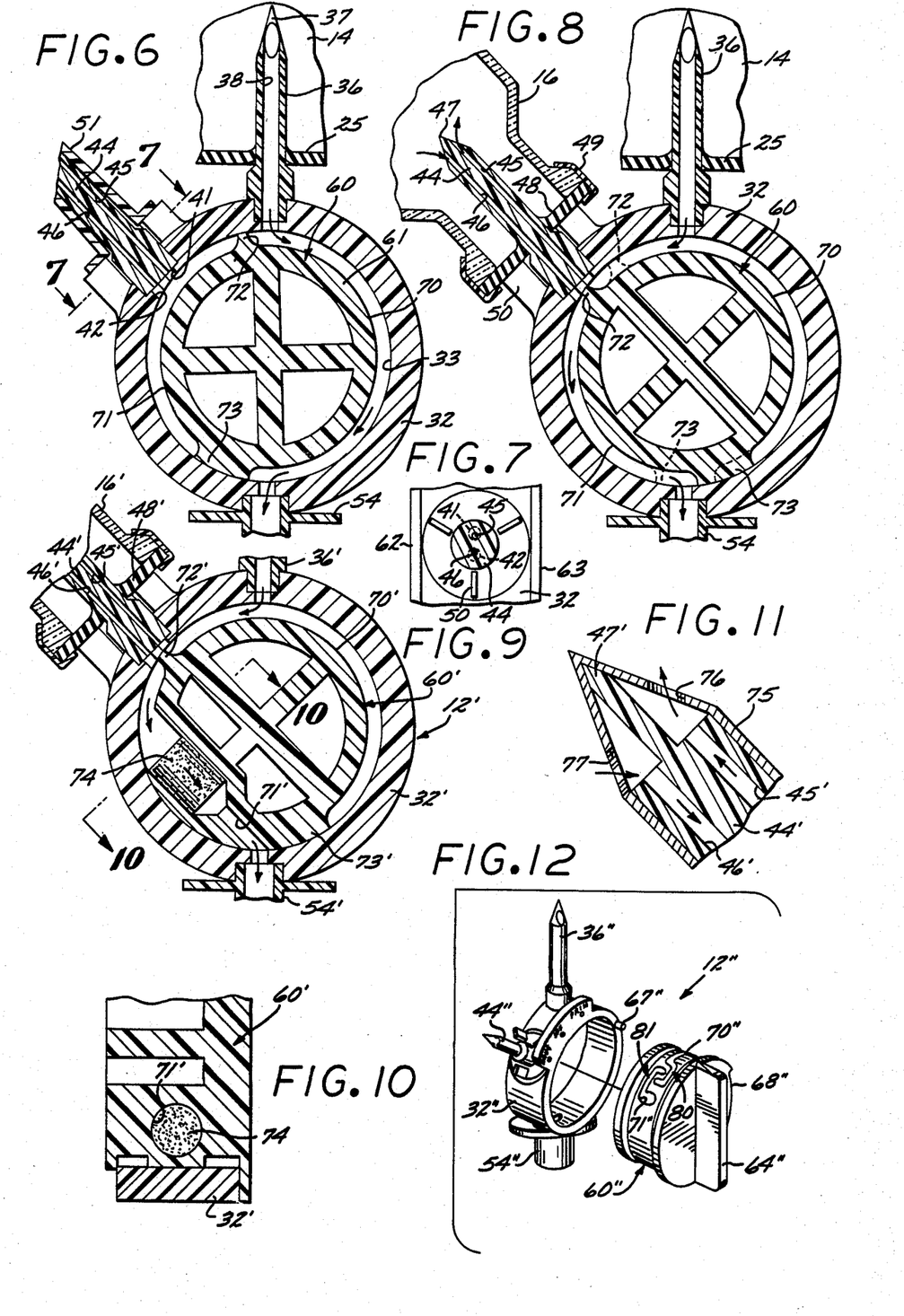
FIG. 6 is an enlarged fragmented transverse vertical section taken generally on the line 6—6 of FIG. 5 with the selector valve in the first position.
FIG. 7 is an enlarged fragmented sectional view taken generally on the line 7—7 of FIG. 6.
FIG. 8 is an enlarged fragmented transverse vertical section generally similar to FIG. 6 but illustrating the selector valve in the second position.
FIG. 9 is an enlarged fragmented transverse vertical section generally similar to FIG. 7 and depicting an alternative selector valve geometry.
FIG. 10 is an enlarged fragmented sectional view taken generally on the line 10—10 of FIG. 9.
FIG. 11 is an enlarged fragmented cross-sectional view illustrating a modified dual path spike geometry for use with the invention.
FIG. 12 is an exploded perspective view illustrating a further alternative form of the selector valve.

A pair of circumferentially closely spaced fluid ports 41 and 42 are also formed in the valve housing 32 to open generally in an upward direction, as shown in FIGS. 6-8. These fluid ports 41 and 42 merge into a common counterbore sized for seated reception of the base end of a secondary spike 44 having a pair of fluid flow paths 45 and 46 aligned respectively over the housing ports 41 and 42. The secondary spike 44, which may be conveniently formed from a molded plastic or the like, extends from the valve housing 32 generally in an upward direction at an angle of about 45 degrees relative to the primary spike 36, and terminates in a pointed free end 47 for pierced passage through the self-sealing resilient member 48 of a cap 49 for the secondary fluid container 16, as viewed in FIG. 8. Conveniently, upstanding wings 50 on the valve housing 32 provide a stop surface which assists in supporting the secondary container 16 when installed upon the secondary spike 44. A protective cap 51 (FIGS. 1 and 6) may be installed snugly over the secondary spike 44 to maintain the sterility thereof when not in use. This cap 51 may be seated onto the uppermost surfaces of the wings 50 as shown in FIG. 6, or the wings 50 can be spaced radially outwardly a greater distance from the spike 44 to define an annulus therebetween into which the cap 51 may be seated.

Figure 4:
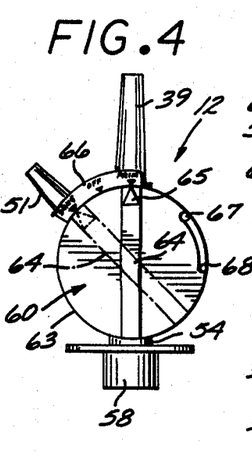
FIG. 4 is an enlarged front elevation view of the selector valve.
Figure 5:
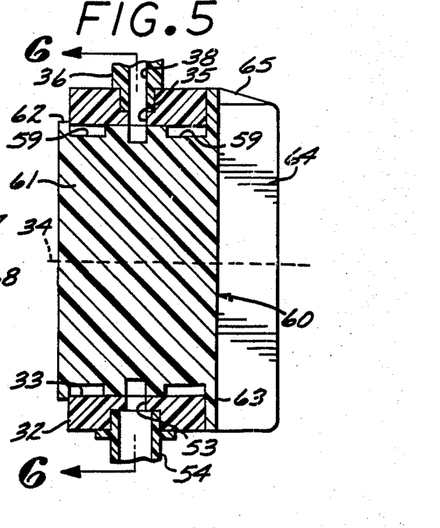
FIG. 5 is an enlarged fragmented vertical section through the selector valve taken generally on the line 5—5 of FIG. 2.

At the lower end of the cylindrical valve housing 32, at a position generally diametrically opposite the inlet port 35, an outlet port 53 is formed in the valve housing 32 including an external counterbore for seated reception of a flanged outlet fitting 54. This outlet fitting 54 may also be formed from molded plastic or the like and includes a tubular lower end for appropriate attachment to the IV set 26. More particularly, with reference to FIG. 1, the tubular lower end of the outlet fitting 54 may be seated within the upper end of the upwardly open drop chamber 28, in which case the fitting 54 may be formed to a include standard drop former (not shown). Alternatively, the outlet fitting 54 may securely receive the upper end of a spike adapter coupling 55 having a central diaphragm 56 designed for seated pierced reception by an upwardly projecting spiked conduit 57 or an alternative drop chamber 28'. A protective cap 58, as shown in FIG. 4, optionally may be carried over the lower end of the outlet fitting 54 until the selector valve 12 is placed in use.

A generally disk-shaped valve insert 60 is rotatable carried within the valve chamber 33 of the valve housing 32 for movement between the primary and secondary positions to control fluid flow through the selector valve 12. More particularly, this valve insert 60 is preferably constructed from a selected molded plastic, such as polyurethane or the like, to have a generally cylindrical valve body 61 with an outside diameter sized for relatively close, substantially fluid-sealed sliding fit with the inside diameter of the cylindrical valve housing 32. An integrally molded rear face ring 62 on the valve insert has a diametric size slightly greater than the valve chamber 33 and is chamfered at its rear outermost edge. With this construction, the valve insert can be pressed rearwardly into the valve chamber 33, with the rear face ring 62 having sufficient resiliency to compress radially and then to snap back to its normal diametric size to abut the rear axial side of the valve housing 32. In this position, a radially enlarged front face plate 63 bears against the axially forward side of the valve housing 32. Circumferential grooves 59 may be formed into the insert to minimize the total sliding contact area between the valve insert and the valve housing 32, thereby facilitating valve insert rotation and further to provide a double-faced fluid seal, as will be described.

A forwardly projecting and diametrically extending indicator bar 64 is formed on the face plate 63 of the valve insert 60 to provide an easily grasped structure for rotating said face plate, wherein the indicator bar 64 has a pointed upper end 65 for registry with index markings on the valve housing. As shown best in FIGS. 1 and 2, these index markings are imprinted upon an upstanding flange 66 formed integrally with the valve housing 32, with the exemplary marking "PRIM" corresponding with the primary or first position of the valve insert and the exemplary marking "DRUG" corresponding with the second valve insert position. An intermediate valve insert position designated illustratively "OFF" may be provided, if desired. A lug 67 on the inboard side of the front face plate 63 projects rearwardly for reception into notches 68 on the valve housing 32 and is respectively oriented to stop the valve insert rotation at the first and second positions, with the notch 68 corresponding with the first position being shown in FIG. 5. Alternatively, other types of valve insert rotational limiting and stop device can be used.

The outside diameter of the valve insert 60 is formed to define a fluid channel network for controlling fluid flow through the selector valve 12 in accordance with selector valve rotational position. More particularly, this fluid channel network is defined by a pair of axially centered and generally semi-circumferentially extending flow grooves 70 and 71 formed in the outer diameter surface of the valve insert 60. As shown best in FIGS. 6 and 8, these flow grooves 70 and 71 extend around opposite sides of the valve insert 60 and are separated from each other at their upper and lower extents, respectively, by upper and lower radial shoulders 72 and 73 sized for fluid-sealed sliding fit with the inside diameter of the valve housing 32. Alternatively, these flow grooves may be defined in part by bores (not shown) drilled or molded through the valve insert, if desired.

In use, the selector valve 12 is connected between the primary fluid container 14 and the fluid administration set 26. More particularly, the protective cap 39 is removed from the primary spike 36 to permit puncture reception thereof through the self-sealing member 25 of the primary fluid container cap 24. The lower outlet fitting 54 is then connected to the drop chamber device 28 of the IV set 26. The valve insert 60 of the selector valve 12 is set initially to the first position in general alignment with the primary spike 36 and the outlet fitting 54, after which the selector valve 12 and IV set 26 are primed with the primary infusion fluid and the catheter (not shown) or the like of the IV set 26 is then installed, for example, intravenously into the patient. The protective cap 51 covering the secondary spike 44 is normally left in place until secondary fluid administration is desired, as will be discussed in more detail.

In the first position, the fluid channel network of the valve insert 60 guides the primary infusion fluid directly from the primary spike 36 to the outlet fitting 54 for supply to the patient. More specifically, as shown in FIG. 6, the arcuate length of the illustrative flow groove 70 in the valve insert 60 is slightly greater than 180 degrees, and the arcuate length of the other illustrative flow groove 71 is somewhat less than 180 degrees. In the first position, the valve insert 60 positions the upper radial shoulder 72 between the primary spike 36 and the secondary spike 44, whereas the lower radial shoulder 73 is positioned between the secondary spike 44 and the lower outlet fitting 54. With this configuration, primary infusion fluid is blocked from direct flow to the secondary spike 44, but instead, is guided through the flow groove 70 to the outlet fitting 54.

When it is desired to infuse a secondary infusion fluid, such as a selected drug solution into the patient, the protective cap 51 is removed from the secondary spike 44 and the secondary fluid container 16 is mounted onto the spike 44 with said spike piercing the resilient self-sealing member 48 of the cap 49 of the fluid container. The valve insert 60 is then rotated to the second position pointing generally toward the secondary spike, as shown in FIG. 8, to modify the orientation of the fluid channel network thereby rerouting the directions of fluid flow through the selector valve 12. More specifically, the upper radial shoulder 72 separating the flow grooves 70 and 71 is rotated to a position between the radially separated fluid ports 41 and 42 underlying the flow paths 45 and 46 of the secondary spike 44, whereas the lower radial shoulder 73 is rotated to a position between the primary spike 36 and the lower outlet fitting 54. This blocks direct passage of the primary infusion fluid 18 to the outlet fitting 54. Instead, the primary infusion fluid 18 is coupled to the fluid port 41 and the flow path 45 for flow into the secondary fluid container 16. Simultaneously, the interior of the secondary fluid container 16 is coupled through the flow path 46 and the fluid port 42 for passage through the flow groove 71 to the outlet fitting 54 for supply to the patient. Accordingly, the secondary container is coupled serially or in-line with the flow path of the primary infusion fluid 18, such that the primary fluid 18 washes into and dilutes the secondary infusion fluid 20 within the secondary fluid container 16 and further carries the secondary infusion fluid 20 through the selector valve and the IV set into the patient. Importantly, when the secondary infusion fluid 20 has been completely infused into the patient, the valve insert 60 may be left in the second position to permit automated resumption of primary fluid infusion flowing through the secondary fluid container to the outlet fitting 54.

If desired, the selector valve insert 60 may also be rotated to an intermediate or third position preventing fluid flow through the selector valve 12. This intermediate position is represented in dotted lines in FIG. 8 with the upper shoulder positioned between the primary spike 36 and the secondary spike 44, and with the lower shoulder 73 blocking any fluid flow downwardly through the outlet fitting 54. Accordingly, the valve insert 60 prevents any discharge fluid flow from the selector valve thereby placing the entire system in an "OFF" condition.

The fluid infusion system 10 of the present invention thus provides a relatively simple, inexpensive, and easy-to-use arrangement for selective administration of primary and/or secondary infusion fluids to a patient. The selector valve 12 advantageous may be provided in the form of an inexpensive disposable product which can be reused for infusing secondary fluids on multiple occasions within the lifecycle of the IV set 26, or the selector valve may be constructed for periodic resterilization and reuse, if desired. When infusion of a selected drug solution or the like is required, the secondary fluid container which may be of a standardized vial size, is installed quickly and easily onto the selector valve and the valve insert 60 is rotatable rapidly to the second position without significantly interrupting fluid flow through the IV set 26, thereby avoiding activation of any infusion system alarms. Moreover, by placement of the selector valve 12 in the infusion system upstream from the underlying drop chamber 28 and vertically below the secondary container 16, any air present in the selector valve 12, particularly within the region of the groove 31 is captured within the secondary container 16 or within the drop chamber 28 to prevent inadvertent infusion thereof into the patient. Further, the diametric size of the valve insert 60 is chosen to provide a substantially leak-free fit with the valve housing 22 in the absence of additional seal components, such as seal rings and the like, with the front and rear face rings on the insert also sealably contacting the housing to provide a double fluid seal in both the forward and rearward directions from the flow grooves 70 and 71.

A variety of modifications and improvements in the fluid infusion system of the present invention will be apparent to those skilled in the art. For example, one alternative selector valve construction is shown in FIGS. 9–11 wherein structural components corresponding with those shown and described in FIGS. 1–8 are designated by common primed reference numerals.

More particularly, a modified selector valve 12' is shown in FIGS. 9 and 10 for selected supply of a primary infusion fluid and/or a secondary infusion fluid to a patient. The selector valve 12' includes a cylindrical valve housing 32' supporting an upwardly projecting primary spike 36', a generally upwardly projecting dual path secondary spike 44' for selected reception into a secondary fluid container 16' and a lower outlet fitting 54' for connection to the patient via an IV set. A valve insert 60' is rotatable between first and second positions, as described with respect to the previous embodiment, and includes upper and lower radial shoulders 72' and 73' for controlling the direction of fluid flow through a flow groove 70' and a modified flow channel 71'. More particularly, the modified fluid flow channel 71' in the valve insert 60' comprises a formed bore having an enlarged inlet end for reception of a porous particle filter 74 of conventional design for separating particles from fluid flowing therethrough.

In use, the modified selector valve 12' operates in a first position as described above with respect to FIGS. 1–8 for primary infusion fluid flow to a patient. In the second position, however, the valve insert 60' is rotated to route the fluid exiting the secondary fluid container 16' through the filter 74 and further through a narrower discharge end of the channel 71' for flow through the outlet fitting 54' and further to the patient. Any particles within the fluid, such as undissolved drug particles from the secondary container 16' are blocked by the filter 74 against flow to the patient unless and until those particles become dissolved within the fluid stream.

As shown in FIG. 11, the secondary spike 44' of the modified selector valve 12' can be adapted for enhancing fluid mixing within the secondary fluid container 16'. More particularly, the flow paths 45' and 46' formed in the secondary spike 44' terminate in squared-off ends separated by an outwardly projecting divider wall defining the pointed free end 47' of the spike. A cap 75 of stainless steel or the like is secured as by press-fitting over the secondary spike 44' and includes a conically pointed tip for puncturing the self-sealing cap member 48' of the secondary fluid container. This conical tip cooperates with the end of the spike 44' to define small collection chambers 78 and 79 at the pointed end of the secondary spike and through which appropriately angled ports may be formed to control fluid flow direction within the secondary fluid container. In particular, a discharge port 76 is formed in one side of the cap 75 such that fluid from the flow path 45' entering the chamber 78 is discharged in an upward direction generally parallel with the primary spike 36' (FIG. 9). Similarly, an inlet port 77 is formed in the other side of the cap 75 for initial inflow of fluid into the chamber 79 in an upward direction generally perpendicular with a central axis of the other flow path 46' prior to downward turning motion of the fluid for entry into the flow path 46'. With this arrangement, fluid flowing into and discharged from the second fluid container 16' is subjected to a substantial swirling action within the secondary fluid container for better mixing, dilution, and maintenance of any drug components in solution form. Moreover, this swirling action insures that substantially all of the secondary infusion fluid is ultimately discharged through the flow path 46' for patient infusion.

A further alternative form of the selector valve for use in a fluid infusion system of the present invention is shown in FIGS. 12–18, wherein components corresponding with those shown and described above with respect to FIGS. 1–11 are identified by common double primed reference numerals. More particularly, as shown, a modified selector valve 12'' includes a valve housing 32'' generally identical with the valve housing 32 described above in combination with a rotatable valve insert 60'' having a modified fluid channel network formed in the outer diameter surface thereof. This modified fluid channel network is designed to permit filling of a secondary fluid container (not shown in FIG. 12) with primary infusion fluid when the valve insert 60'' is rotated to an intermediate or third position identified illustratively in FIG. 12 as the "FILL" position. In this intermediate position, however, the fluid channel network prevents flow of fluid through an outlet fitting 54'' to the patient, thereby permitting a dried or particulate pharmaceutical, such as a freeze-dried drug compound, within a vacuum secondary fluid container to be reconstituted to solution form utilizing primary infusion fluid for a brief time interval prior to administration to the patient.

As shown best in FIG. 12, the illustrative valve housing 32'' supports an upwardly projecting primary spike 36'' for reception into a container of primary infusion fluid and a dual path secondary spike 44'' projecting generally upwardly at an angle of about 45 degrees for reception into an appropriate secondary container, such as a pharmaceutical vial of standardized size containing under vacuum a drug compound requiring reconstitution with fluid prior to administration to a patient. The valve insert 60" is receivable into the cylindrical valve housing 32" and is rotatable manually by grasping a forward indicator bar 64" and rotating the insert between predetermined rotational positions defined by a stop pin 67" on the valve housing for receiving a lug (not shown in FIG. 12) on the valve insert.

The outer diameter surface of the modified valve insert 60" includes a generally semi-circumferential groove 70" formed to extend from an upper region of the valve insert around one side to a diametrically opposite or lower valve insert region. The upper region of this groove 70" terminates in a generally U-shaped segment identified by arrow 80. Importantly, this U-shaped segment 80 is formed in spaced overlapping relation with an upper generally U-shaped groove segment 81 which is coupled at its end opposite the groove 70" to a flow channel 71" formed through the valve insert and terminating in a lower end near the outlet fitting 54". The lower end of this channel 71" is circumferentially spaced a short distance from the lower end of the groove 70" by a radial shoulder 73 (FIG. 13) formed integrally with the valve insert 60". If desired, an appropriate filter 74" (FIG. 13) may be installed along the channel 71" to entrap particulate, such as undissolved drug particles.

Figures 13, 14:
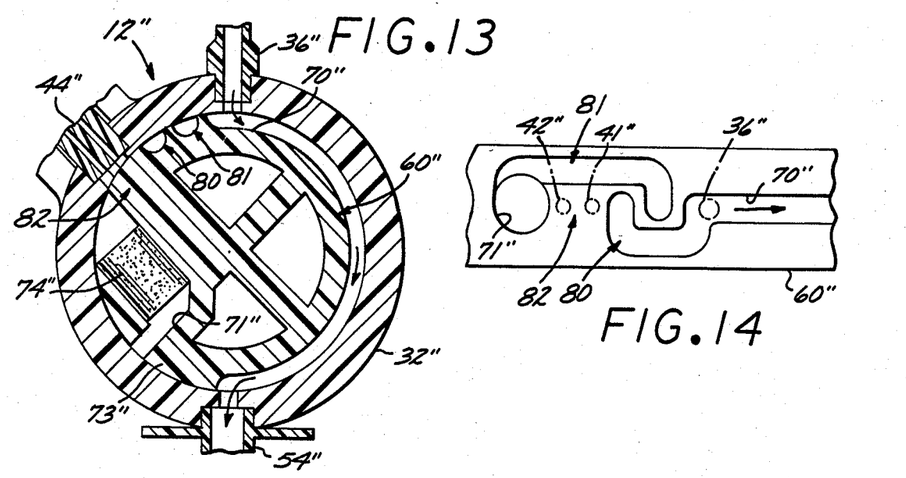
FIG. 13 is an enlarged fragmented transverse vertical section of the selector valve shown in FIG. 12, with the selector valve in a first position for administration of a primary infusion fluid to a patient.
FIG. 14 is a schematic developed plan view representation of fluid flow through the selector valve in the first position.

In use, the modified selector valve 12" is included within a fluid administration system of the type depicted in FIGS. 2 and 3 with the primary spike 36" protruding upwardly into a primary infusion fluid container and the lower outlet fitting 54' coupled to the patient via an appropriate IV set. In normal operation, the valve insert 60" is rotated to orient the indicator bar 64" in a first position indicated by the exemplary designation "PRIM" on the valve housing 32". In this first position, as shown in FIGS. 13 and 14, the flow groove 70" has its upper end in open communication with the primary spike 36" and its lower end in flow communication with the outlet fitting 54" for direct flow of primary infusion fluid to the patient. Importantly, the radial shoulder 73" on the valve insert 60" is oriented rotationally between the dual path secondary spike 44" and the outlet fitting 54" to prevent flow communication therebetween. Moreover, a portion of the outer diameter surface of the valve insert 60", identified by arrow 82, is aligned with the secondary spike 44 to block the associated fluid ports 41" and 42" in the valve housing 32".

When administration of a selected pharmaceutical compound is desired, a container of the compound is installed upon the secondary spike 44' in the same manner as described previously with respect of the selector valve 12. This container may carry the compound in a dried or particulate state or other form requiring reconstitution with fluid prior to administration to the patient. In this case, the secondary container preferably comprises a vacuum container for drawing primary infusion fluid into the container interior when the valve insert 60" is rotated to the intermediate or "FILL" position.

Figures 15, 16:
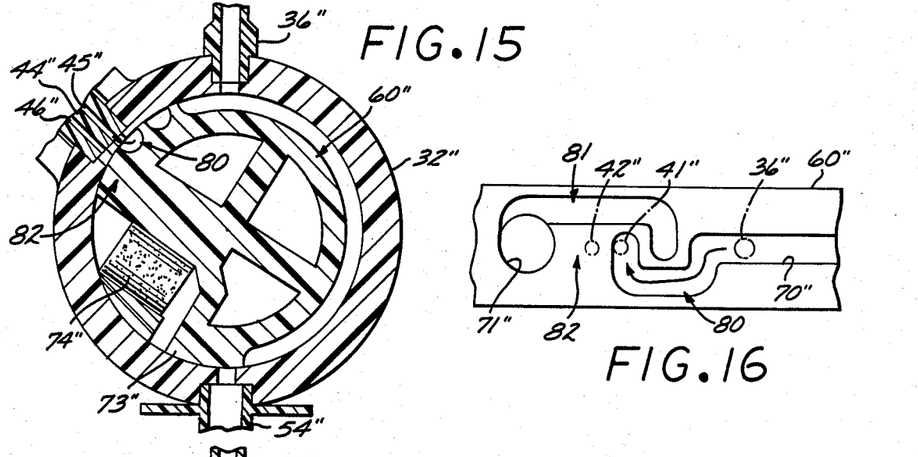
FIG. 15 is an enlarged fragmented transverse vertical section generally similar to FIG. 13 and illustrating the selector valve in a third or intermediate position.
FIG. 16 is a schematic developed plan view representation of fluid flow through the selector valve in the intermediate position.

More particularly, as depicted in FIGS. 15 and 16, rotation of the valve insert 60" to the intermediate position displaces the lower radial shoulder 73" to a position blocking fluid flow to the outlet fitting 54. Simultaneously, such valve insert rotation moves the distal end of the U-shaped groove segment 80 into flow communication with the fluid port 41" which in turn couples the primary fluid flow for entry into the secondary container through the inlet flow path 45" of the secondary spike 44"'. The vacuum within the secondary container draws the primary infusion fluid into the secondary container for reconstituting the drug compound therein, while the outlet flow path 46" of the secondary spike remains blocked by the underlying outer diameter surface portion 82 of the valve insert.

Figures 17, 18:
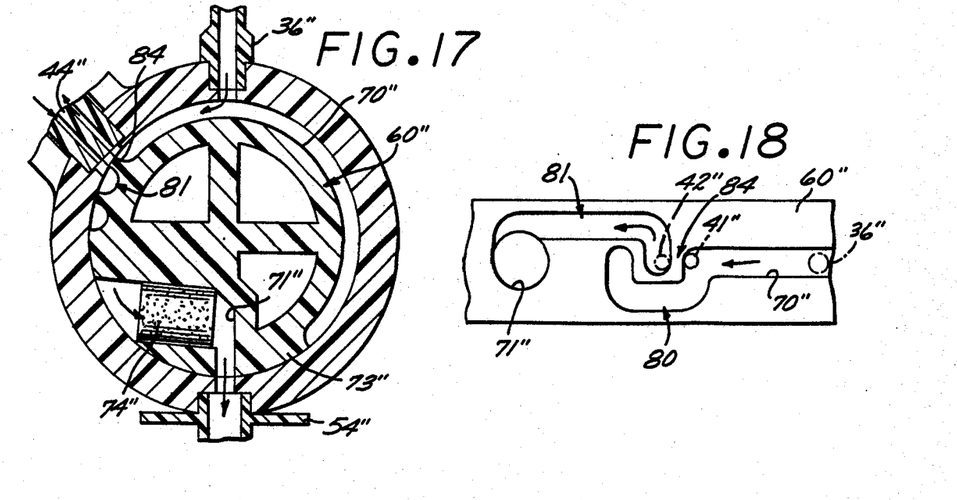
FIG. 17 is an enlarged fragmented transverse vertical section generally similar to FIG. 12 and illustrating the selector valve in a second position for administration of a secondary infusion fluid to the patient.
FIG. 18 is a schematic developed plan view representation of fluid flow through the selector valve in the second position.

After a brief reconstitution interval typically on the order of a few seconds, the valve insert 60" is rotatable to the second or illustrative "DRUG" position for administration of the now-reconstituted drug compound in solution form to the patient. In this position, as shown in FIGS. 17 and 18, the valve insert 60" rotates the lower shoulder 73" to a position circumferentially between the primary spike 36" and the outlet fitting 54" to prevent direct fluid flow therebetween. Instead, the primary infusion fluid enters the flow groove 70" for flow toward the U-shaped groove segment 80, the proximal end of which is in flow communication with the housing port 41' to permit fluid flow through the inlet path 45" of the secondary spike. The primary infusion fluid washes through the secondary container and returns to the selector valve through the outlet path 46" of the secondary spike and enters the distal end of the U-shaped groove segment 81 aligned beneath the housing flow port 42", with a portion 84 of the valve insert periphery preventing direct flow between the ports 41" and 42'. The fluid flows further through this groove segment 81 into the flow channel 71" which is aligned with the outlet fitting 54" to permit fluid flow to the patient. When administration of the drug compound is complete, the valve insert 60" may be left in the second position for resumed infusion of the primary fluid, or the valve insert may be switched back to the first position for primary fluid infusion.

Further modifications and improvements to the fluid infusion system and selector valve described herein are believed to be apparent to those of ordinary skill in the art. For example, the various fluid flow paths through the selector valve can be formed with any desired grooves or bore geometry consistent with manufacturing processes. Moreover, if desired, the valve housing of the selector valve can be formed integrally with the primary and secondary spikes as well as the outlet fitting to reduce the number of requisite components. Still further, although flow paths 45 and 46 of circular cross section are shown in the illustrative drawings, these flow paths may be formed with generally back-to-back D-shaped cross sections for increased flow areas, if desired. Accordingly, no limitation on the invention is intended by way of the foregoing description, except as set forth in the appended claims.

What is claimed is:

1. A fluid infusion system for selective administration of a primary infusion fluid and a secondary infusion fluid to a patient, comprising:

a selector valve including a valve housing, a hollow primary spike projecting generally upwardly from said valve housing for connection to a supply of the primary infusion fluid, a dual flow path secondary spike projecting generally upwardly from said valve housing for connection to a supply of the secondary infusion fluid, an outlet fitting on said valve housing, and a valve member carried by said valve housing and cooperating therewith to define a fluid channel network for controlling fluid flow through said primary and secondary spikes to said outlet fitting;

said valve member being movable between a first position orienting the fluid channel network for direct fluid flow communication of said primary spike with said outlet fitting and for blocking fluid flow communication of said secondary spike with said primary spike and said outlet fitting, and a second position orienting the fluid channel network for direct fluid flow communication between said primary spike and one of the secondary spike flow paths and between the other of the secondary spike flow paths and said outlet fitting and for blocking direct flow communication between said primary spike and said outlet fitting; and infusion fluid administration set means for guiding fluid flow through said outlet fitting to the patient.

2. The fluid infusion system of claim 1 wherein said outlet fitting defines an outlet port opening generally downwardly from said valve housing.

3. The fluid infusion system of claim 1 including a first protective cap for removably covering said primary spike.

4. The fluid infusion system of claim 1 including a second protective cap for removably covering said secondary spike.

5. The fluid infusion system of claim 1 including a third protective cap for removably covering said outlet fitting.

6. The fluid infusion system of claim 1 further including a primary container carrying the supply of the primary infusion fluid and having a self-sealing cap for pierced reception of said primary spike, and a secondary container for the secondary infusion fluid and having a self-sealing cap for pierced reception of said secondary spike.

7. The fluid infusion system of claim 1 wherein said secondary spike projects generally upwardly from said valve housing at an angle of about forty-five degrees with respect to said primary spike.

8. The fluid infusion system of claim 7 wherein said valve housing further includes means for supporting a container for the secondary infusion fluid when said secondary spike is connected to the supply of the secondary infusion fluid.

9. A fluid infusion system for selective administration of a primary infusion fluid and a secondary infusion fluid to a patient, comprising:

a selector valve including a valve housing, a hollow primary spike projecting generally upwardly from said valve housing for connection to a supply of the primary infusion fluid, a dual flow path secondary spike projecting generally upwardly from said valve housing for connection to a supply of the secondary infusion fluid, an outlet fitting on said valve housing, and a valve member carried by said valve housing and cooperating therewith to define a fluid channel network for controlling fluid flow through said primary and secondary spikes to said outlet fitting;

said valve housing including a valve chamber having a generally cylindrical shape, said primary and secondary spikes projecting generally upwardly from said valve housing in closely spaced positions about the circumference of said valve chamber, said movable valve member comprising a generally cylindrical valve insert receivable with relatively close sliding fit into said valve chamber and having first and second fluid flow channels formed therein defining the fluid channel network and shoulder means for separating said first and second fluid channels from each other, said valve insert being rotatable generally about a central axis of said valve chamber between a first position with said first channel in open communication with said primary spike and said outlet fitting and with said shoulder means blocking flow communication of said secondary spike with said outlet fitting and said primary spike, and a second position with said first channel in open communication with said primary spike and one of the secondary spike flow paths and with said second channel in open communication with the other secondary spike flow path and said outlet fitting, said shoulder means blocking direct fluid flow through said valve chamber between the secondary spike flow paths and further blocking direct fluid flow between said primary spike and said outlet fitting when said valve insert is in said second position; and infusion fluid administration set means for guiding fluid flow through said outlet fitting to the patient.

10. The fluid infusion system of claim 9 wherein said valve housing has a circumferentially closely spaced pair of fluid ports formed therein in alignment respectively with the secondary spike flow paths.

11. The fluid infusion system of claim 9 wherein said first and second channels in said valve insert comprise a pair of generally semi-circumferential grooves formed in said valve insert, said shoulder means including first and second shoulders disposed respectively between opposite adjacent ends of said grooves.

12. The fluid infusion system of claim 9 including filter means mounted along said second channel.

13. The fluid infusion system of claim 9 wherein said valve insert is movable to a third position intermediate said first and second positions with said shoulder means blocking fluid flow through said outlet fitting.

14. The fluid infusion system of claim 13 wherein said first channel is oriented in open communication between said primary spike and one of the secondary spike flow paths when said valve insert is in said third position, said shoulder means blocking the other of the secondary spike flow paths to prevent fluid flow therethrough when said valve insert is in said third position.

15. The fluid infusion system of claim 14 further including a vacuum container for removable mounting onto said secondary spike.

16. The fluid infusion system of claim 9 further including position indicator means reacting between said valve insert and said valve housing for releasably retaining said valve insert in said first and second positions when said insert is respectively rotated thereto.

17. The fluid infusion system of claim 1 wherein said valve member is movable to a third position blocking fluid flow through said outlet fitting.

18. The fluid infusion system of claim 1 further including indicia means for visibly indicating the position of said valve member.

19. The fluid infusion system of claim 1 wherein the dual flow paths in said secondary spike are formed generally in parallel with each other, and further including a pointed cap fitted over the upper end of said secondary spike and including a pair of ports aligned generally and respectively with the upper ends of said flow paths, one of said ports being oriented to guide fluid discharged from one of said flow paths in a generally upward direction and away from the other of said flow paths, and the other of said ports being oriented for passage of fluid generally in an upward direction prior to entry of the fluid into the upper end of the other of said flow paths.

20. The fluid infusion system of claim 19 wherein said pointed cap is formed from stainless steel.

21. The fluid infusion system of claim 9 wherein said valve insert comprises a generally cylindrical body having said first and second fluid flow channels formed therein, a rear face ring having an outside diametric size slightly greater than the inside diametric size of said valve chamber, and a front face ring having an outside diametric size greater than said valve chamber diametric size, said valve insert being sufficiently resilient for reception of said rear face ring through said valve chamber to a position abutting a rear axial side of said valve housing with said front face ring abutting a front axial side of said valve housing.

22. The fluid infusion system of claim 21 wherein said first and second flow channels are defined at least in part by flow grooves recessed into the outer diameter surface of said valve body, said valve body outer diameter surface being sized for substantially fluid-sealed fit with an inner diameter surface of said valve housing and said front and rear face rings abutting respectively the front and rear axial sides of said valve housing with a substantially fluid-sealed fit, said valve body further including in its outer diameter surface a pair of circumferential recessed seal grooves disposed at axial positions forward and rearward of said flow grooves.

23. A fluid infusion system for selective administration of a primary infusion fluid and a secondary infusion fluid to a patient, comprising:
 a selector valve including a valve housing defining a valve chamber, first means for coupling said valve chamber to a supply of the primary infusion fluid within a primary container, second means for coupling said valve chamber to a supply of the secondary infusion fluid within a secondary container, and an outlet port; and
 third means for coupling fluid flow through said outlet port to the patient;
 said selector valve further including a movable valve member within said valve chamber and cooperating with said valve housing to define a fluid channel network, said valve member being movable between a first position orienting the fluid channel network for coupling the primary infusion fluid for direct flow from said first means through said valve chamber to said outlet port and for preventing fluid flow from said second means to said outlet port, and a second position reorienting the fluid channel network for coupling the primary infusion fluid for flow from said first means through a portion of said valve chamber into and through said second means and second container followed by flow through another portion of said valve chamber to said outlet port.

24. The fluid infusion system of claim 23 wherein said second means comprises a dual flow path spike.

25. The fluid infusion system of claim 24 wherein said valve member is further movable to a third position coupling the primary infusion fluid for flow from said first means through a portion of said valve chamber and through one of the flow paths of said spike into the second container, said valve member including means for blocking fluid flow through the other of the spike flow paths and said outlet port when said valve member is in said third position.

26. The fluid infusion system of claim 23 wherein said valve member is movable to a third position, said valve member including means for blocking fluid flow through said outlet port when said valve member is in said third position.

27. A selector valve for use in a fluid infusion system for selective administration of a primary infusion fluid and a secondary infusion fluid to a patient, said selector valve comprising:
 a valve housing defining a valve chamber and an outlet port for discharge of fluid from said valve chamber;
 a hollow primary spike projecting generally upwardly from said valve housing for connection to a primary container of the primary infusion fluid, said primary spike defining an open conduit for flow of the primary infusion fluid into said valve chamber;
 secondary spike means projecting generally upwardly from said valve housing for connection to a secondary container of the secondary infusion fluid, said secondary spike means defining a first flow path for inflow of fluid from said valve chamber into the second container and a second flow path for outflow of fluid from the second container into said valve chamber; and
 a valve member movably carried by said valve housing generally within said valve chamber and defining a fluid channel network for controlling fluid flow through said valve chamber;
 said valve member being movable between a first position orienting the fluid channel network for direct fluid flow from said primary spike through said valve chamber to said outlet port and for blocking said first and second flow paths of said secondary spike means from flow communication with said primary spike and said outlet port, and a second position orienting the fluid channel network for routing flow of the primary infusion fluid from said primary spike through a portion of said valve chamber and further through said first flow path for passage into the second container and for outflow therefrom through said second flow path into another portion of said valve chamber for flow to said outlet port.

28. The selector valve of claim 27 wherein said outlet port opens generally in a downward direction and said secondary spike means comprises a secondary spike oriented generally at an angle of about forty-five degrees with respect to said primary spike.

29. A selector valve for use in a fluid infusion system for selective administration of a primary infusion fluid and a secondary infusion fluid to a patient, said selector valve comprising:
 a valve housing defining a valve chamber and an outlet port for discharge of fluid from said valve chamber;
 a hollow primary spike projecting generally upwardly from said valve housing for connection to a primary container of the primary infusion fluid, said primary spike defining an open conduit for flow of the primary infusion fluid into said valve chamber;
 secondary spike means projecting generally upwardly from said valve housing for connection to a second container of the secondary infusion fluid, said secondary spike means defining a first flow path for inflow of fluid from said valve chamber into the second container and a second flow path for outflow of fluid from the second container into said valve chamber; and a valve member movably carried by said valve housing generally within said valve chamber and defining a fluid channel network for controlling fluid flow through said valve chamber;

said outlet port opening generally in a downward direction and said secondary spike means comprising a secondary spike oriented generally at an angle of about forty-five degrees with respect to said primary spike;

said valve chamber defined by said valve housing having a generally cylindrical shape, said primary and secondary spikes projecting generally upwardly from said valve housing in closely spaced positions about the circumference of said valve chamber, said movable valve member comprising a generally cylindrical valve insert receivable with relatively close sliding fit into said valve chamber and having first and second fluid flow channels formed therein defining the fluid channel network and shoulder means for separating said first and second fluid channels from each other, said valve insert being rotatable generally about a central axis of said valve chamber between a first position with said first channel in open communication with said primary spike and said outlet port and with said shoulder means blocking flow communication of said secondary spike with said outlet port and said primary spike, and a second position with said first channel in open communication with said primary spike and said first flow path of said secondary spike and with said second channel in open communication with said second flow path of said secondary spike and said outlet port, said shoulder means blocking direct fluid flow through said valve chamber between said first and second flow paths and further blocking direct fluid flow between said primary spike and said outlet port when said valve insert is in said second position.

30. The selector valve of claim 29 wherein said valve housing has a circumferentially closely spaced pair of fluid ports formed therein in alignment respectively with said first and second flow paths in said secondary spike.

31. The selector valve of claim 29 wherein said first and second channels in said valve insert comprises a pair of generally semi-circumferential grooves formed in said valve insert, said shoulder means including first and second shoulders disposed respectively between opposite adjacent ends of said grooves.

32. The selector valve of claim 29 including filter means mounted along said second channel.

33. The selector valve of claim 29 wherein said valve insert is movable to a third position intermediate said first and second positions with said shoulder means blocking fluid flow through said outlet port.

34. The selector valve of claim 33 wherein said first channel is oriented in open communication between said primary spike and said first flow path of said secondary spike when said valve insert is in said third position, said shoulder means blocking said second flow path of said secondary spike to prevent fluid flow therethrough when said valve insert is in said third position.

35. The selector valve of claim 29 wherein said valve insert comprises a generally cylindrical body having said first and second fluid flow channels formed therein, a rear face ring having an outside diametric size slightly greater than the inside diametric size of said valve chamber, and a front face ring having an outside diametric size greater than said valve chamber diametric size, said valve insert being sufficiently resilient for reception of said rear face ring through said valve chamber to a position abutting a rear axial side of said valve housing with said front face ring abutting a front axial side of said valve housing.

36. The selector valve of claim 35 wherein said first and second flow channels are defined at least in part by flow grooves recessed into the outer diameter surface of said valve body, said valve body outer diameter surface being sized for substantially fluid-sealed fit with an inner diameter surface of said valve housing and said front and rear face rings abutting respectively the front and rear axial sides of said valve housing with a substantially fluid sealed fit, said valve body further including in its outer diameter surface a pair of circumferential recessed seal grooves disposed at axial positions forward and rearward of said flow grooves.

37. A selector valve for use in a fluid infusion system for selective administration of a primary infusion fluid and a secondary infusion fluid to a patient, said selector valve comprising:

a generally cylindrical valve housing defining a generally cylindrical valve chamber having a central axis oriented generally on a horizontal plane;

a hollow primary spike projecting generally upwardly from said valve housing for connection to a primary container of the primary infusion fluid, said primary spike defining an open conduit for flow of the primary infusion fluid into said valve chamber;

an outlet fitting opening generally downwardly from said valve housing for discharge of fluid from said valve chamber;

a secondary spike projecting generally upwardly from said valve housing from a position spaced circumferentially about said valve housing a short distance from said primary spike, said secondary spike being for connection to a secondary container of the secondary infusion fluid and defining a first flow path for inflow of fluid from said valve chamber into the second container and a second flow path for outflow of fluid from the second container into said valve chamber;

a generally cylindrical valve insert having an outer diameter surface sized for relatively close sliding fit into said valve chamber of said valve housing, said valve insert defining a fluid channel network and being rotatable generally about said central axis for reorienting said fluid channel network to control fluid flow through said valve chamber; and means for retaining said valve insert generally within said valve chamber for rotation about the central axis thereof;

said valve insert fluid channel network including a first channel, a second channel, and shoulder means separating said first and second channels from direct flow communication with each other;

said valve insert being rotatable to a first position with said first channel in open communication with said primary spike and said outlet fitting to permit fluid flow therebetween and with said shoulder means preventing fluid flow from said secondary spike to said outlet fitting and said primary spike;

said valve insert being rotatable to a second position with said shoulder means blocking direct fluid communication through said valve chamber between said first and second flow paths of said secondary spike and between said primary spike and said outlet fitting, with said first channel in open flow communication with said primary spike and said first flow path of said secondary spike to permit fluid flow therebetween, and with said second channel in open communication between said second flow path of said secondary spike and said outlet fitting to permit fluid flow therebetween.

38. The selector valve of claim 37 wherein said valve insert includes a forwardly projecting indicator bar, said bar being aligned generally with said primary spike and generally with said secondary spike when said valve insert is in said first and second positions, respectively.

39. The selector valve of claim 37 wherein said valve housing further includes means for removably supporting the secondary container.

40. The selector valve of claim 37 including filter means mounted along said second channel.

41. The selector valve of claim 37 wherein said valve insert is movable to a third position intermediate said first and second positions with said shoulder means blocking fluid flow through said outlet fitting.

42. The selector valve of claim 41 wherein said first channel is oriented in open communication between said primary spike and one of the secondary spike flow paths when said valve insert is in said third position, said shoulder means blocking the other of the secondary spike flow paths to prevent fluid flow therethrough when said valve insert is in said third position.

43. The selector valve of claim 42 wherein said first and second channels comprise at least in part first and second grooves formed in the outer diameter surface of said valve insert with overlapping, generally U-shaped groove segments.

44. The selector valve of claim 37 further including position indicator means reacting between said valve insert and said valve housing for releasably retaining said valve insert in said first and second positions when said insert is respectively rotated thereto.

* * * * *